United States Patent
Zhu

(10) Patent No.: US 9,220,894 B1
(45) Date of Patent: Dec. 29, 2015

(54) OVERSHOOT WAVEFORM IN MICRO CURRENT THERAPY

(71) Applicant: TrioWave Technologies, Fremont, CA (US)

(72) Inventor: Huiyou Zhu, Fremont, CA (US)

(73) Assignee: TrioWave Technologies, Fremont, CA (US)

( * ) Notice: Subject to any disclaimer, the term of this patent is extended or adjusted under 35 U.S.C. 154(b) by 0 days.

(21) Appl. No.: 14/823,992

(22) Filed: Aug. 11, 2015

Related U.S. Application Data

(60) Provisional application No. 62/037,029, filed on Aug. 13, 2014.

(51) Int. Cl.
*A61N 1/32* (2006.01)
*A61N 1/36* (2006.01)

(52) U.S. Cl.
CPC ............ *A61N 1/326* (2013.01); *A61N 1/36021* (2013.01); *A61N 1/36046* (2013.01)

(58) Field of Classification Search
CPC  A61N 1/326; A61N 1/36021; A61N 1/36046
See application file for complete search history.

(56) References Cited

U.S. PATENT DOCUMENTS

| | | | | |
|---|---|---|---|---|
| 4,105,023 | A * | 8/1978 | Marchese et al. | A61B 5/04004 600/510 |
| 6,035,236 | A * | 3/2000 | Jarding et al. | A61N 1/32 607/53 |
| 6,275,735 | B1 * | 8/2001 | Jarding et al. | A61N 1/32 607/53 |
| 6,535,767 | B1 | 3/2003 | Kronberg | |
| 7,909,861 | B2 | 3/2011 | Balachandran et al. | |

* cited by examiner

*Primary Examiner* — Catherine Voorhees
(74) *Attorney, Agent, or Firm* — Alex Y. Nie; Sheppard Mullin Richter & Hampton LLP

(57) ABSTRACT

Systems and methods are provided to generate an waveform for micro current therapy. The waveform includes overshoot signals overlaid on constant currents and is capable of stimulating cells or nerves to achieve healing. The system can include an oscillator configured to generate a reference signal, a pulse wave generator to generate a pulse waveform signal based on the reference signal, an overshoot generator to generate an overshoot signal based on the reference signal, and an output module to generate a composite output waveform signal based on the overshoot signal and the pulse waveform signal, wherein the composite output waveform includes one or more pulses having one or more overshoots that extend a width of each of the pulses. The system can be adjusted by a user depending on the disease, condition, or preference of the user.

20 Claims, 3 Drawing Sheets

OVERSHOOT WAVEFORM IN MICRO CURRENT THERAPY

CROSS-REFERENCE TO RELATED PATENT APPLICATIONS

This application claims the benefit under 35 U.S.C. §119 (e) of U.S. Provisional Application 62/037,029, filed Aug. 13, 2014, which is incorporated herein by reference in its entireties and for all purposes.

BACKGROUND

This disclosure relates to systems and methods for generating waveform outputs suitable for micro current therapy to human subjects. The waveform outputs can stimulate excitable cells, such as nerve cells, in a human body, for effective and fast healing.

Micro current electrotherapy devices known in the art typically apply constant current from square waves to stimulate a portion of a human body. This kind of waveforms usually are presented in either monophasic or biphasic forms to stimulate cellular physiology and growth with low amplitude and in low frequency to provide therapeutic benefits.

SUMMARY

Square waveforms that generate constant current are generally operated in low voltage amplitudes and are discovered to be less effective in exciting cells or nerves. Although the voltage and frequency can be adjusted to improve stimulation, such adjustment may offset the therapeutic benefits.

The present disclosure provides systems and methods for generating an output waveform that achieves enhanced benefits of micro current based electrotherapy. The output waveform includes overshoot signals overlaid on constant currents and is capable of stimulating cells or nerves to achieve healing. In one embodiment, the system includes an oscillator configured to generate a reference signal, a pulse wave generator to generate a pulse waveform signal based on the reference signal, an overshoot generator to generate an overshoot signal based on the reference signal, and an output module to generate a composite output waveform signal based on the overshoot signal and the pulse waveform signal, wherein the composite output waveform includes one or more pulses having one or more overshoots that extend a width of each of the pulses. The system can be adjusted by a user depending on the disease, condition, or preference of the user.

In one embodiment, provided is a system comprising an oscillator configured to generate a reference signal; a pulse wave generator configured to generate a pulse waveform signal based on the reference signal, the pulse waveform signal having a first frequency from 0.1 Hz to 200 Hz and a first amplitude between 1 $\mu$A and 200 $\mu$A; and an overshoot generator configured to generate an overshoot signal based on the reference signal, the overshoot signal having a second frequency from 1 Hz to 5000 Hz and a second amplitude between 1 $\mu$A and 600 $\mu$A, the second frequency being at least twice that of the first frequency; an output module configured to generate a composite output waveform signal based on the overshoot signal and the pulse waveform signal, the composite output waveform comprising one or more pulses having one or more overshoots that extend a width of each of the pulses.

In some aspects, the pulse waveform signal is digital. In some aspects, the overshoot signal is digital. In some aspects the composite output waveform signal is analog.

In some aspects, the pulse waveform signal and the overshoot signal are digital, and the output module comprises: a mixer configured to generate a digital intermediate waveform signal based on the pulse waveform signal and the overshoot signal; and a digital-to-analog converter configured to generate an analog intermediate waveform signal based on the digital intermediate waveform signal, the composite output waveform signal being based on the digital intermediate waveform signal. In some aspects, the output module further comprises a level shifter configured to adjust a level of the analog intermediate waveform before the composite output waveform signal is produced based on the analog intermediate waveform. In some aspects, the output module further comprises an amplifier configured to adjust an amplitude of the analog intermediate waveform before the composite output waveform is produced based on the analog intermediate waveform.

In some aspects, each of the pulses has at least two overshoots. In some aspects, the composite output waveform signal is capable to induce a cell to enter a polarization stage. In some aspects, the cell is a muscle cell or nerve cell. In some aspects, the overshoots in the composite output waveform signal each has a rising edge that reaches a peak within 2 ms. In some aspects, the overshoots in the composite output waveform signal each has a falling edge that is less steep than the rising edge.

In some aspects, the second frequency of the overshoot signal is between 10 Hz and 2000 Hz. In some aspects, the second amplitude of the overshoot signal is between 5 $\mu$A and 50 $\mu$A. In some aspects, the pulse waveform signal is a square waveform signal. In some aspects, the first frequency of the pulse waveform signal is between 0.2 Hz and 100 Hz.

In some aspects, the system further comprises an input device for taking an input from a human user and a processor to adjust the first frequency, first amplitude, second frequency, or second amplitude based on the input.

Also provided, in one embodiment, is a method for improving healing of a human subject in need thereof, comprising connecting a system the disclosure to the subject and configuring the system to apply a composite output waveform signal to the subject suitable for exciting a cell in the subject, thereby improving healing of the human subject. In some aspects, the method further comprises receiving an input from the subject at the system and adjusting the Composite output waveform signal. In some aspects, the subject suffers from a pain, age-related macular degeneration, a wound, or tendon injury.

BRIEF DESCRIPTION OF THE DRAWINGS

Provided as embodiments of this disclosure are drawings which illustrate by exemplification only, and not limitation, wherein.

It will be recognized that some or all of the figures are schematic representations for exemplification and, hence, that they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Figure 1:
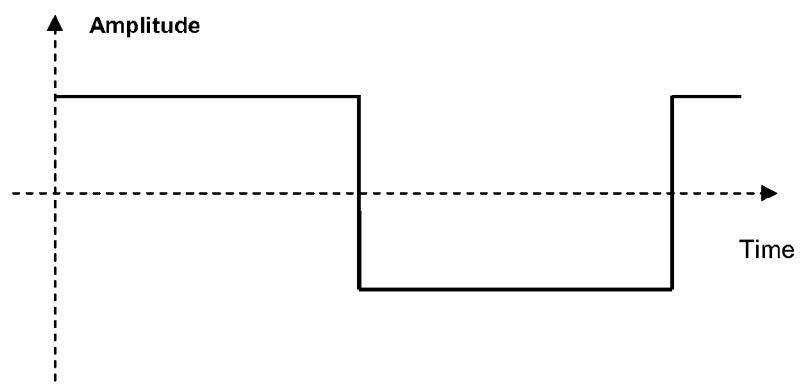
FIG. 1 illustrates a conventional square waveform.

FIG. 1 illustrates a conventional square waveform that has been used in micro current-based electrotherapy. The polarity can be mono-phasic (positive or negative), or biphasic (both positive and negative phases) by alternating the polarity in low frequency.

Figure 2:
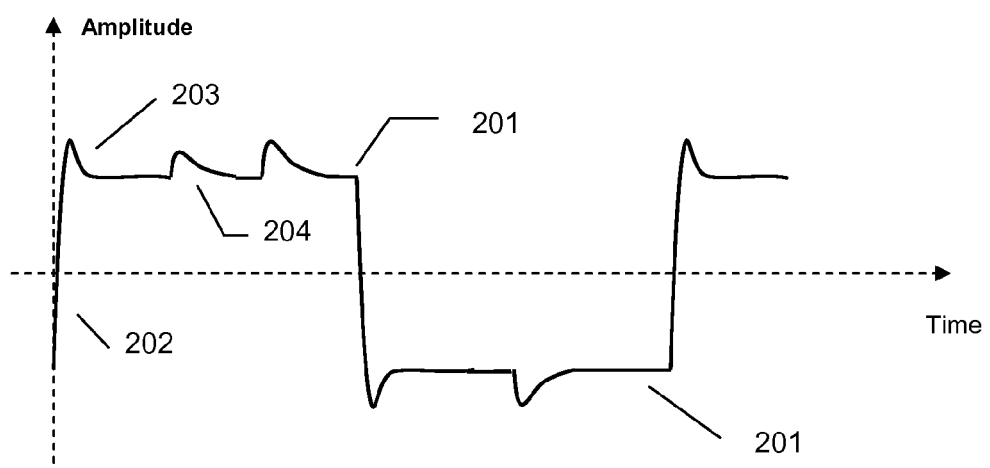
FIG. 2 illustrates an output composite waveform that includes a square waveform overlaid with overshoot signals.

FIG. 2 shows a diagram of a square waveform (or more generally a pulse waveform) with overshoot signals that improve the ability to stimulate cells to achieve therapeutic benefits. The base pulse waveform is similar to what is shown in FIG. 1 and can be mono-phasic or biphasic. Each phase can be substantially constant, that is, the variation (e.g., the standard deviation of the amplitude within each phase) is within 10% (or 5%) of the amplitude.

The amplitude of the base pulse waveform (201) can be adjusted, and is in general from 1 µA to 200 µA, or alternatively from 5 µA to 100 µA, from 20 µA to 80 µA, from 30 µA to 60 µA or from 30 µA to 50 µA. 202 shows a rapid rising phase of overshoot signal that could go over threshold potential for cell or nerve polarization; 203 shows a slow falling phase and resting phase of overshoot signal and decay into base pulse wave stage 201. Overshoot signal can occur multiple times 204 (e.g., at least 2, at least 3, at least 4, at least 5 times) in a single phase with a frequency resonating with the type of cell and nerve.

The frequency of the base pulse wave can also be adjusted, for instance, by a user through an input module. In general, the frequency is from 0.1 Hz to 200 Hz. In some aspects, the frequency is greater than 0.1 Hz, 0.2 Hz, 0.5 Hz, 1 Hz, 2 Hz, 5 Hz, 10 Hz or 20 Hz. In some aspects, the frequency is lower than 200 Hz, 180 Hz, 150 Hz, 100 Hz, 90 Hz, 80 Hz, 70 Hz, 60 Hz, 50 Hz, 40 Hz, 30 Hz, 20 Hz, 10 Hz or 5 Hz.

The base pulse wave can be bisphasic (as shown in FIG. 2) or mono-phasic waveforms. In some aspects, the base pulse wave is a square wave.

Figure 4:
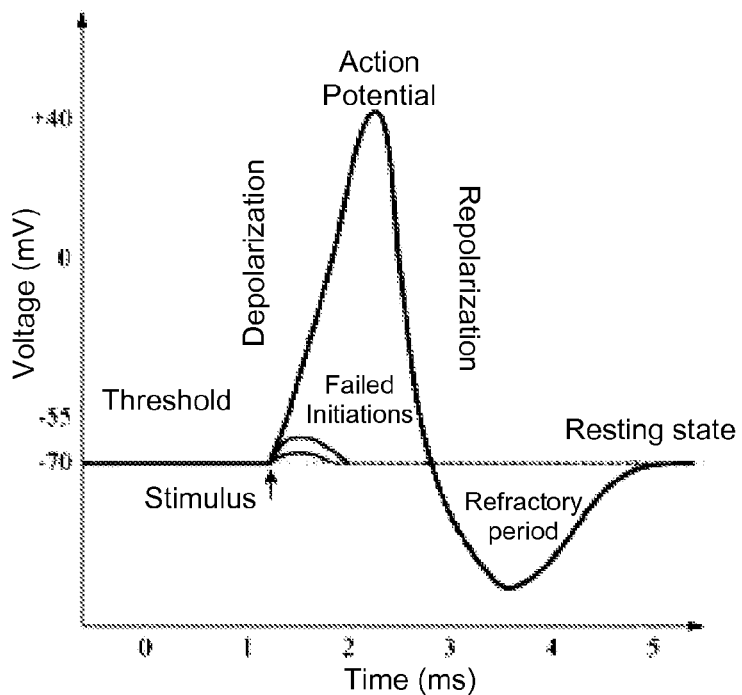
FIG. 4 illustrates that to induce a cell or nerve to enter a polarization stage, certain voltage potential change over a threshold (usually between −20 mV and −65 mV depending on type of cell or nerve) is needed.

The waveforms of the present disclosure can be used to generate voltage potentials suitable for stimulating excitable cells in a human body so that the cell enters a polarization stage. To trigger a cell like a nerve cell to enter such stage, a voltage potential change has to be large enough to reach a threshold (usually between −20 mV and −65 mV depending on type of cell or nerve), as illustrated in FIG. 4.

Rather than increasing the amplitude of the pulse wave, the present technology adds an overshoot to the base pulse wave to ensure that the amplitude of the peaks are large enough to reach the threshold.

Figure 5:
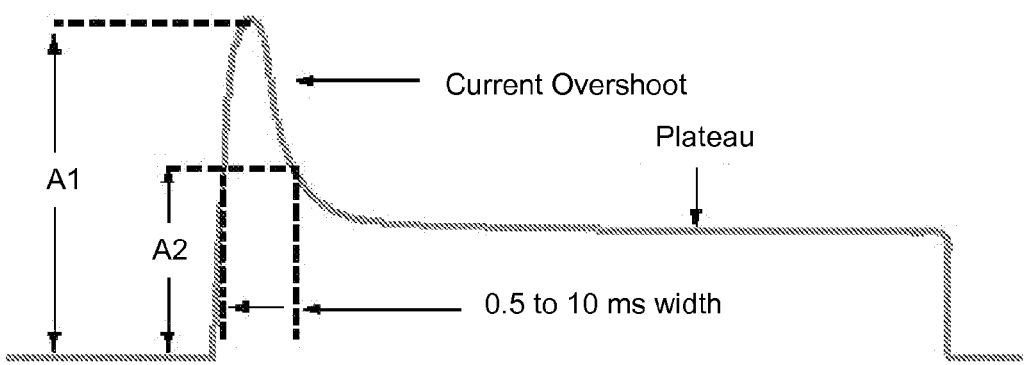
FIG. 5 illustrates a shape of an overshoot signal used in the present disclosure.

FIG. 5 illustrates an overshoot signal that is suitable for generating a composite outcome waveform. For instance, the overshoot signal has a rising edge (left of the peak) that is steeper than a falling edge (right of the peak). The rising edge, in some aspects, reaches the peak within 2 ms, or alternatively within 0.1 ms, 0.2 ms, 0.3 ms, 0.4 ms, 0.5 ms, 0.6 ms, 0.7 ms, 0.8 ms, 0.9 ms, 1 ms, 1.2 ms, 1.5 ms, or 1.8 ms.

In some aspects, the failing edge shows a plateau, which can last from 0.5 ms to 10 ms. In some aspects, the time span of the falling edge (from peak to back to a pulse phase) is at least twice (or alternatively 3×, 4×, 5×, 10×) the time span of the rising edge (from a pulse phase to peak). The gradual falling of the overshoot amplitudes helps to achieve the resting state of polarization and avoid another threshold triggering before the previous polarization stage is completed.

In some aspects, there is a resting period between each overshoot signal. In one aspect, the resting period is at least 0.5 ms, or alternatively at least 1 ms, 1.5 ms, 2 ms, 3 ms, 4 ms or 5 ms. In one aspect, the resting period is not longer than 20 ms, 10 ms, 5 ms, 4 ms, 3 ms or 2 ms. In one aspect, the resting period is at least 50% of the time span of the overshoot signal, or alternatively at least 75%, 100%, 150%, 2×, 3×, 4× or 5× of the time span of the overshoot signal. In one aspect, the resting period is not longer than 2×, 3×, 4×, 5×, 10× or 20× of the time span of the overshoot signal.

The frequency, shape and amplitude of the overshoot signals can be adjusted. The peak amplitude, in general, is adequate to genera a 0 to +/−100 mV voltage potential, and in some aspects between −20 mV and −65 mV depending on type of cell or nerve. In some aspects, the amplitude of the overshoot signal is between 1 µA and 600 µA. In one aspect, the amplitude of the overshoot signal is greater than 1 µA, 2 µA, 3 µA, 4 µA, 5 µA, or 10 µA. In one aspect, the amplitude of the overshoot signal is less than 500 µA, 400 µA, 300 µA, 200 µA, 100 µA, 90 µA, 80 µA, 70 µA, 60 µA, 50 µA, 40 µA, 30 µA, 20 µA, or 10 µA. In some aspects, the amplitude of the overshoot signal is at least 10%, or alternatively at least 20%, 30%, 40%, 50%, 75%, 100%, 150%, 200% or 250% of the amplitude of the base pulse signal. In some aspects, the amplitude of the overshoot signal is not greater than 10 times, 9 times, 8 times, 7 times, 6 times, 5 times, 4 times, 3 times, or twice of the amplitude of the base pulse signal.

The frequency of the overshoot signals can be greater than that of the base pulse waveform, so that each phase of the base pulse waveform is superimposed (or overlaid) with at least an overshoot signal. In one aspect, the frequency is at least 1 Hz, or alternatively at least 2 Hz, 5 Hz, 10 Hz, 15 Hz, 20 Hz, 30 Hz, 40 Hz, 50 Hz, 100 Hz, 150 Hz or 200 Hz. In some aspects, the frequency is not greater than 5 KHz, 2 KHz, 1 KHz, 500 Hz, 200 Hz, 150 Hz or 100 Hz.

In some aspects, the frequency, amplitude, shape, resting period, of any of the above waveforms or signals can be adjusted on the fly during a therapy. The adjustment can be automatic or triggered by input from a user.

Figure 3:
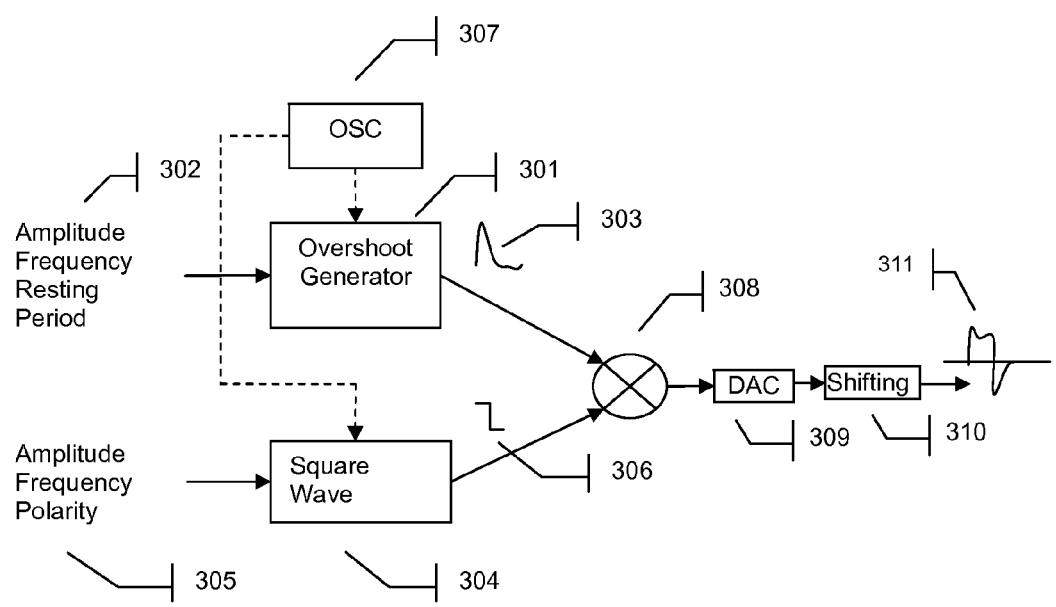
FIG. 3 illustrates a system that can be configured to generate an output waveform of one embodiment of the present disclosure.

FIG. 3 illustrates a system useful for generating an output waveform of the present disclosure. Overshoot Generator 301 represents a micro-controller based component that is programmable to produce digitized overshoot signal according to requested parameters 302, and output digitized overshoot 303. Pulse Wave Generator 304 is a programmable component that takes requested parameters 305 to generate digitized pulse wave signal 306. Both Overshoot Generator 301 and Pulse Wave Generator 304 are connected to Oscillator 307 for signal synchronization. Both digitized signals 303 and 306 will be sent to component 308 for composition, and sent to digital-to-analog converter (DAC)/Shifting 309 to convert into analog signal. By shifting the analog signal in 310 to output expected overshoot waveform as 311.

An oscillator herein is an electronic circuit that synchronizes the generation of pulse waves and overshoot waves in a digital format. A digital-to-analog converter (DAC) is a function that converts digital data (usually binary) into an analog signal (current, voltage, or electric charge). An analog-to-digital converter (ADC) performs the reverse function.

In some aspects, the system further includes wires and/or electrodes to connect to the skin or other organs of a human subject so as to apply an output waveform to the user. in some aspects, the system further includes an input module or device that takes an input from the user. The input can then be used to start, stop or adjust the waveform applied to the user. In one aspect, the input module is wired to the system and in another aspect, the input module communicates with the system wirelessly. In some aspects, the input module includes a graphic user interface. In some aspects, the system includes a processor to take the input and implement adjustments.

Methods of micro current electrotherapy are also provided, in some embodiments. The output waveforms that can be generated from the systems are applied to a human subject. Various parameters of the waveforms can be adjusted to suit the user or the particular disease or condition that the user has, such as back pain, arthritis at the knee, or wound on the skin.

A micro current electrotherapy entails sending relatively weak electrical signals into the body of an individual in need of the therapy. Such therapies apply small (e.g., between 1 and 50 microampere) electrical currents to nerves using electrodes placed on the skin. Micro current electrotherapies can be used in treatments for pain, age-related macular degeneration, wound healing, and tendon repair, without limitation. Many micro current treatments concentrate on pain and/or speeding healing and recovery. Micro current treatments are commonly used by professional and performance athletes with acute pain and/or muscle tenderness as they are drug-free and non-invasive, thus avoiding testing and recovery issues. They can also be used as a cosmetic treatment.

Generation of Biphasic Waveforms

Biphasic waveforms in some embodiments of the disclosure can be generated with apparatuses and methods known in the art. In a particular embodiment, the disclosure provides a new system and method for generating biphasic waveform energy-efficiently. Further details of this new system and method (the "biphasic system") are provided in U.S. patent application Ser. No. 14/823,978, entitled "Systems and Methods for Generating Biphasic Waveforms," filed Aug. 11, 2015, which claims benefit under 35 U.S.C. §119(e) of U.S. Provisional Application 62/084,202, filed Nov. 25, 2014. The content of each of these applications is incorporated to the present disclosure by reference in its entirety.

The biphasic system uses a constant current source and/or a constant current sink with one power source to generate biphasic waveforms. In one example, a positive, constant current is generated from a single constant current source, and then applied to either end of an output workload in an alternating manner, such as at a predefined frequency.

In another example, a constant current source is used to generate a positive phase, and a constant current sink is used to generate a negative phase. An alternating adoption of these two phases, therefore, gives rise to the application of a biphasic waveform on an output workload.

One embodiment of the biphasic system is a system for generating a biphasic waveform to a workload, comprising: a constant current source configured to generate a constant current; a first switch having a first end and a second end, wherein the first end switches between the current source and the ground; a second switch having a third end and a fourth end, wherein the third end switches between the current source and the ground; and a microcontroller configured to set the first switch and the second switch to alternate between configurations (a) and (b): (a) the first end connects to the current source and the third end connects to the ground; and (b) the first end connects to the ground and the third end connects to the current source, wherein, when a workload is connected to the second end of the first switch and the fourth end of the second switch, configuration (a) allows the constant current to be applied to the workload from the first switch, through the workload and the second switch, to the ground, and configuration (b) allows the constant current to be applied to the workload from the second switch, through the workload and the first switch, to the ground, thereby applying a biphasic waveform with alternating phases to the workload.

Another embodiment of the biphasic system is a system for generating a biphasic waveform to a workload, comprising: a constant current source configured to generate a constant first current; a current sink; a switch having a first end and a second end, wherein the second end switches between a power supply and the ground; and a microcontroller configured to set the current source, the current sink, and the switch to alternate between configurations (a) and (b): (a) the current sink is deactivated or disconnected and the switch connects to the ground; and (b) the current source is deactivated or disconnected and the switch connects to the power supply, wherein, when a workload is connected to the second end of the switch and the current source or the current sink, configuration (a) allows the constant first current to be applied to the workload from the current source, through the workload and the switch, to the ground, and configuration (b) allows the current sink to absorb a second current from the power supply, through the switch and the workload, thereby applying a biphasic waveform with alternating phases to the workload.

A "biphasic waveform" is a current waveform that includes primarily two phases appearing in an alternating manner. In one aspect, one of the phases is positive and the other negative. In another aspect, both phases are positive or negative, but one has a higher amplitude than the other. In one aspect, both phases are constant or substantially constant. In another aspect, the phases are asymmetric such as one with a positive of square wave and a negative in sine wave. In another aspect, the phases are symmetric such as sine waves.

In a particular embodiment, the biphasic waveform comprises a constant positive phase and a constant negative phase having the same or substantially the same amplitudes. Nevertheless, it is readily appreciated that the devices and methods of the present disclosure can be used to generate any biphasic waveforms, including symmetric and asymmetric waveforms.

In one embodiment, the biphasic system includes a microcontroller, a current source, two control switches, and optionally a convertor. In some instances, the current source is a constant current source, generating positive, constant current.

A "current source" is an electronic circuit that delivers an electric current which is independent of the voltage across it. A current source can be an independent current source that delivers a constant current. A dependent current source, by contrast, delivers a current which is proportional to some other voltage or current in the circuit.

Current sources are different from voltage sources. A theoretical voltage source would have a zero ohm output impedance in series with the source. A real-world voltage source has a very low, but non-zero output impedance: often much less than 1 ohm. By contrast, a current source provides a constant current, as long as the load connected to the source terminals has sufficiently low impedance. An ideal current source would provide no energy to a short circuit and approach infinite energy and voltage as the load resistance approaches infinity (an open circuit). An ideal current source has an infinite output impedance in parallel with the source. A real-world current source has a very high, but finite output impedance.

The microcontroller can control the operation of a constant current source, such as sending a digital waveform to the constant current source or turn it on or off. Further, the microcontroller regulates the control switches, optionally through a controlling convertor that converts digital control signal from the microcontroller to the control pins of two switches (first and second switches).

The two switches, for instance, can be multiplexer (or mux) type switches. Each switch can include a control pin that is controlled by the microcontroller. The first has two terminals, one connected to an output workload when in use, and the other switching between the output terminal of the current source and the ground. Likewise, the second switch has two terminals, one connected to an output workload when in use (the opposite side from the terminal of the first switch), and the other switching between the output terminal of the current source and the ground.

When in operation, the device is connected to an output workload, through two terminals of both switches. The microcontroller controls both switches to set in two different configurations in an alternating manner.

In configuration (a), the first switch connects with the current source and the second switch connects to the ground. Therefore, in this configuration, the current from the current source goes through the first switch, the workload, the second switch, and to the ground.

In configuration (b), the first switch connects to the ground and the second switch connects with the current source. Therefore, in this configuration, the current from the current source goes through the second switch, the workload, the first switch, and to the ground.

When the microcontroller controls the switches to alternate between configurations (a) and (b), therefore, the workload receives the current from two opposite directions, resulting in an application of a biphasic waveform on the workload.

In another embodiment, the biphasic system includes a microcontroller, a current source, a control switch, a positive supply voltage (VDD), and a current sink. In some instances, the current source is a constant current source, generating positive, constant current. In some instances, the current sink is a constant current sink, that generates a constant current by absorbing currents from the VDD.

The microcontroller can control the operation of the current source and the current sink. Further, the microcontroller regulates the switch.

The switch, for instance, can be multiplexer (or mux) type switches. The switch can include a control pin that is controlled by the microcontroller. The switch has two terminals, one connected to an output workload when in use, and the other switching between the ground and the VDD.

When in operation, the device is connected to an output workload which, at one end, connects to the current source and the current sink, and at the other end, connects to the switch. Accordingly, the microcontroller can control the switch to set in two different configurations in an alternating manner.

In configuration (a), the switch connects with the ground. Optionally, at this configuration, the microcontroller turns off the current sink and/or voltage supply VDD. Therefore, in this configuration, the current from the current source goes through the workload and the switch, and to the ground.

In configuration (b), the switch connects to the voltage supply VDD. Optionally, at this configuration, the microcontroller turns off the current source. Therefore, in this configuration, a current arises from VDD, going through the workload into the current sink.

When the microcontroller controls the switch to alternate between configurations (a) and (b), therefore, the workload either receives a current from the current source or from the voltage source absorbed by the current sink. These currents come from two opposite directions, resulting in an application of a biphasic waveform on the workload.

The amplitudes of the currents generated by the current sources can be adjusted as needed. For instance, for therapeutic use, the amplitude can in general be from 1 μA to 200 μA, or alternatively from 5 μA to 100 μA, from 20 μA to 80 μA, from 30 μA to 60 μA or from 30 μA to 50 μA.

The frequency of the biphasic waveform can also be adjusted depending on needs. For instance, the frequency (i.e., the alternating frequency) can be from 0.1 Hz to 200 Hz. In some aspects, the frequency is greater than 0.1 Hz, 0.2 Hz, 0.5 Hz, 1 Hz, 2 Hz, 5 Hz, 10 Hz or 20 Hz. In some aspects, the frequency is lower than 200 Hz, 180 Hz, 150 Hz, 100 Hz, 90 Hz, 80 Hz, 70 Hz, 60 Hz, 50 Hz, 40 Hz, 30 Hz, 20 Hz, 10 Hz or 5 Hz.

The waveforms of the present disclosure can be used to generate voltage potentials suitable for stimulating excitable cells in a human body so that the cell enters a polarization stage. To trigger a cell like a nerve cell to enter such stage, a voltage potential change has to be large enough to reach a threshold (usually between −20 mV and −65 mV depending on type of cell or nerve).

Progressive Signal Adjustment

Battery-driven stimulators for electrotherapy usually equip with a small battery to generate specified current waveforms applied to human body for stimulation. Such current waveforms can easily get into a saturated status due to high bio-impedance and low battery power. The present disclosure also provides systems and methods that overcome this problem. In one embodiment, the waveform (e.g., the base pulse waveforms of the overshoot) is adjusted according to feedbacks taken from a patient to reduce or avoid saturation. In another embodiment, the system includes a detachable battery pack that enables convenient use and charging of a battery in the battery pack.

Further details of such system and method are provided in U.S. patent application Ser. No. 14/823,990, entitled "Signal Adjustment for Electrotherapy," filed Aug. 11, 2015, which claims benefit under 35 U.S.C. §119(e) of U.S. Provisional Application 62/043,894, filed Aug. 29, 2014, and U.S. patent application Ser. No. 14/823,982, entitled "Battery Pack for Electrotherapy Devices," filed Aug. 11, 2015, which claims benefit under 35 U.S.C. §119(e) of U.S. Provisional Application 62/043,912, filed Aug. 29, 2014. The content of each of these applications is incorporated to the present disclosure by reference in its entirety.

For a battery that has a preset working voltage range, the current of its output waveforms is restricted by bio-impedance that usually is high, such as 200 KOhm or above, at an early stage, and gradually comes down to an acceptable level, 2 KOhm or less, after minutes or hours. This bio-impedance is carried by electrodes that apply stimulation signals to human body to gradually establish ionic channels to reduce bio-impedance.

A conventional electrotherapy device typically does not take the influence of the bio-impedance into consideration, but simply generates a predetermined waveform that can result in a saturated output waveform (i.e., exceeding working power range), or an invalid output waveform for electrotherapy.

It is discovered by the instant inventor that progressive adjustment of a current waveform can be used to reduce or even prevent occurrence of saturated waveform outputs. The adjustment can take the voltage between the electrodes as input when the electrodes are applied on the skin or body of a human patient. The voltage can be directly measured or derived from other parameters, as further described below.

One objective of the adjustment is to gradually increase the voltage within a suitable range at an appropriate pace. For instance, if the determined voltage is below the upper limit of the range, the system then increases the amplitude of the waveform output by a certain interval. The voltage determination can be repeated at a desired frequency, until the voltage reaches or exceeds the upper limit, at which point the amplitude is reduced to a base level. Afterwards, the voltage determination can continue; so will the increase of the amplitude after each determination.

An example electrical circuit suitable for implementing such progressive adjustment includes a micro controller that includes at least a waveform generator such as a pulse wave generator (e.g., a square wave generator), a processor, and memory that embeds program code for carrying out desired control of the waveform generator. The micro controller is connected to two electrodes (first and second) that output generated current waveforms to a bio impedance (e.g., in a patient body). The current waveform path, as shown, starts from the micro controller, the first electrode, the bio impedance to the second electrode, and back to the micro controller. A analog-to-digital convertor (ADC) can take instruction from the micro controller to gather voltage potentials from the electrodes.

A. Initialization

A $1^{st}$ step of the progressive adjustment initializes the process at which point the following parameters can be set: (a) voltage determination schedule (e.g., a constant time interval), (b) voltage upper limit, (c) maximum and minimum amplitudes, and (d) amplitude increase interval.

The voltage determination schedule, in one aspect, can be a fixed schedule such as repeating the determination at a constant time interval. In another aspect, the interval can increase or decrease where needed. In yet another aspect, the schedule includes a rule for setting the schedule on the fly. For instance, the schedule can be adjusted depending on the determined voltage. For example, when the voltage is close to the upper limit, the determination can be carried out more frequently.

The voltage upper limit can be a fixed value, or set with a user profile, user preference, user input or by the system. Likewise, the maximum and minimum amplitudes for the waveform output can initialized. The amplitude increase interval can be a constant number or determined according to the voltage upper limit, and/or the maximum and minimum amplitudes.

The amplitude of the waveform can have a range from 1 μA to 100 mA, in some aspects. Alternatively, the minimum amplitude can be 2 μA, 3 μA, 4 μA, 5 μA, 10 μA, 20 μA, 30 μA, 50 μA or 100 μA. In some aspects, the maximum amplitude can be 100 μA, 150 μA, 200 μA, 250 μA, 300 μA, 400 μA, 500 μA, 1 mA, 5 mA, 10 mA, 20 mA, 50 mA, 60 mA or 100 mA.

In some aspects, the waveform has a frequency from 0.1 Hz to 200 Hz. In one aspect, the frequency is at least 0.1 Hz, or at least 0.2 Hz, 0.5 Hz, 1 Hz, 5 Hz, 10 Hz or 20 Hz. In one aspect, the frequency is not higher than 500 Hz, 400 Hz, 300 Hz, 200 Hz, 100 Hz, or 50 Hz.

In some aspects, the time interval is at least 5 seconds, or at least 10, 20, 30, 40, 50, or 60 seconds. In some aspects, the time interval is not longer than 30 seconds, or not longer than 60 seconds, 2 minutes, 3 minutes, 4 minutes, 5 minutes or 10 minutes.

In some aspects, the amplitude increase interval is at least 1 μA, or alternatively at least 2 μA, 3 μA, 4 μA, 5 μA, 10 μA, 20 μA, 50 μA, or 100 μA. In some aspects, the amplitude increase interval is not greater than 100 μA, 150 μA, 200 μA, 250 μA, 300 μA, 400 μA, 500 μA, 1 mA, 5 mA, or 10 mA.

In some aspects, the voltage upper limit is at least 1000 mV, 2000 mV, 3000 mV, 4000 mV, 5000 mV. In some aspects, the voltage upper limit is not higher than 5000 mV, 7000 mV, 9000 mV, 10,000 mV, 12,000 mV or 15,000.

At the $2^{nd}$ step, the waveform generator generates a current waveform with the minimum amplitude.

B. Voltage Determination

At the $3^{rd}$ step, the voltage between the electrodes can be determined by ADC sampling, which represents a product of current waveform and bio-impedance. Alternatively, the voltage can be computed from the amplitude and ADC sampling of the bio-impedance.

C. Adjustment

At the $4^{th}$ step, the determined voltage is compared to the voltage upper limit. If the voltage is close to, equal to, or over the upper limit, then the system adjusts the waveform generation to decrease its output's amplitude ($5^{th}$ step). In one aspect, the amplitude is decreased to a base amplitude level (e.g., the minimum amplitude set at the $1^{st}$ step).

If the voltage is lower than the upper limit, then the system adjusts the waveform generation to increase its output's amplitude ($8^{th}$ step) by the increase interval set at the step. In some aspects, a $7^{th}$ step is included to ensure that the amplitude does not exceed the maximum amplitude allowed by the system. Due to unpredictable changes of bio-impedance from electrodes, continuous monitoring of the current waveform is preferred to ensure that voltage is in a desired working range. In either scenario, the system will continue to monitor the voltage ($6^{th}$ step).

The voltage upper limit, in some aspects, can be dynamically changed. For instance, at the $4^{th}$ step, the microcontroller can measure the battery voltage range from the battery pack. Then, the measured battery voltage range can be used to adjust the voltage upper limit. For instance, if the measured battery voltage range has shifted downwards, then the voltage upper limit can be reduced too, by, e.g., 0.05, 0.1 or 0.2 volt, or by certain percentage (e.g., 1%, 2%, 5%, 10%).

Battery Pack

Another embodiment of the present disclosure provides an electrotherapy device that includes a battery pack which is detachably connected to a stimulation pack that includes a waveform generator and control circuits. Without limitation, the stimulation pack can include a microprocessor, digital and analog circuits such as waveform generator, memory, IO pin, oscillator, and/or ADC and DAC.

In one embodiment, the electrotherapy device includes two detachably connected packs (or enclosures), a battery pack and a stimulation pack. The stimulation pack contains at least an electric signal (waveform) generator configured to generate an electric signal and a controller configured to control the generation of the electric signal. The stimulation pack can be connected to a first electrode and to a first connector each of which is in electric communication with the signal generator.

The battery pack can contain at least a battery holder for holding a battery, which holder includes a positive contact and a negative contact. The battery pack, in one aspect, further includes a charging and protection circuit configured to prevent overdrain and overcharge of the battery and a battery indicator configured to indicate a status of the battery. Like the stimulation pack, the battery pack can also be connected to a second electrode and to a second connector each in electric communication with the battery or the charging and protection circuit. In some embodiments, the device further includes a battery, such as a rechargeable battery, in the battery holder.

The first connector and the second connector can be detachably connected to enable electric communication between the signal generator and the charging and protection circuit. Further, the first electrode and the second electrode have a maximum distance of at least 25 cm (or 30 cm, 40 cm, 50 cm, 100 cm, 200 cm, 250 cm, or 300 cm) such that they can be placed on different locations of the body of a patient.

In some aspects, each of the packs can be connected to the corresponding connector through an electric wire. In one aspect, one of the connectors can be directly disposed on the pack.

Although the discussions above may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure. Such variations will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed here. For example, the terms "comprising", "including," containing," etc. shall be read expansively and without limitation. Additionally, the terms and expressions employed here have been used as terms of description and not of limitation; hence, the use of such terms and expressions does not evidence and intention to exclude any equivalents of the features shown and described or of portions thereof. Rather, it is recognized that various modifications are possible within the scope of the disclosure claimed.

By the same token, while the present disclosure has been specifically disclosed by preferred embodiments and optional features, the knowledgeable reader will apprehend modification, improvement and variation of the subject matter embodied here. These modifications, improvements and variations are considered within the scope of the disclosure.

The disclosure has been described broadly and generically here. Each of the narrower species and subgeneric groupings falling within the generic disclosure also form part of the disclosure. This includes the generic description of the disclosure with a proviso or negative limitation removing any subject matter from the genus, regardless of whether or not the excised material is described specifically.

Where features or aspects of the disclosure are described by reference to a Markush group, the disclosure also is described thereby in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Although the disclosure has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A system comprising:
an oscillator configured to generate a reference signal;
a pulse wave generator configured to generate a pulse waveform signal based on the reference signal, the pulse waveform signal having a first frequency from 0.1 Hz to 200 Hz and a first amplitude between 1 µA and 200 µA; and
an overshoot generator configured to generate an overshoot signal based on the reference signal, the overshoot signal having a second frequency from 1 Hz to 5000 Hz and a second amplitude between 1 µA and 600 µA, the second frequency being at least twice that of the first frequency;
an output module configured to generate a composite output waveform signal based on the overshoot signal and the pulse waveform signal, the composite output waveform comprising one or more pulses having one or more overshoots that extend a width of each of the pulses.

2. The system of claim 1, wherein the pulse waveform signal is digital.

3. The system of claim 1, wherein the overshoot signal is digital.

4. The system of claim 1, wherein the composite output waveform signal is analog.

5. The system of claim 1, wherein the pulse waveform signal and the overshoot signal are digital, and the output module comprises:
a mixer configured to generate a digital intermediate waveform signal based on the pulse waveform signal and the overshoot signal; and
a digital-to-analog converter configured to generate an analog intermediate waveform signal based on the digital intermediate waveform signal, the composite output waveform signal being based on the digital intermediate waveform signal.

6. The system of claim 5, wherein the output module further comprises a level shifter configured to adjust a level of the analog intermediate waveform before the composite output waveform signal is produced based on the analog intermediate waveform.

7. The system of claim 5, wherein the output module further comprises an amplifier configured to adjust an amplitude of the analog intermediate waveform before the composite output waveform is produced based on the analog intermediate waveform.

8. The system of claim 1, wherein each of the pulses has at least two overshoots.

9. The system of claim 1, wherein the composite output waveform signal is capable to induce a cell to enter a polarization stage.

10. The system of claim 9, wherein the cell is a muscle cell or nerve cell.

11. The system of claim 9, wherein the overshoots in the composite output waveform signal each has a rising edge that reaches a peak within 2 ms.

12. The system of claim 11, wherein the overshoots in the composite output waveform signal each has a falling edge that is less steep than the rising edge.

13. The system of claim 1, wherein the second frequency of the overshoot signal is between 10 Hz and 2000 Hz.

14. The system of claim 1, wherein the second amplitude of the overshoot signal is between 5 µA and 50 µA.

15. The system of claim 1, wherein the pulse waveform signal is a square waveform signal.

16. The system of claim 11, wherein the first frequency of the pulse waveform signal is between 0.2 Hz and 100 Hz.

17. The system of claim 1, further comprising an input device for taking an input from a human user and a processor to adjust the first frequency, first amplitude, second frequency, or second amplitude based on the input.

18. A method for improving healing of a human subject in need thereof, comprising connecting a system of claim 1 to the subject and configuring the system to apply a composite output waveform signal to the subject suitable for exciting a cell in the subject, thereby improving healing of the human subject.

19. The method of claim 18, further comprising receiving an input from the subject at the system and adjusting the composite output waveform signal.

20. The method of claim 18, wherein the subject suffers from a pain, age-related macular degeneration, a wound, or tendon injury.

\* \* \* \* \*